United States Patent [19]

Arsenault

[11] Patent Number: 6,112,753
[45] Date of Patent: Sep. 5, 2000

[54] DENTAL FLOSS

[76] Inventor: Peter Arsenault, 65 Butterfield St., Lowell, Mass. 01854

[21] Appl. No.: 09/356,126

[22] Filed: Jul. 17, 1999

[51] Int. Cl.$^7$ ................................................ A61C 15/00
[52] U.S. Cl. ........................................ 132/323; 132/321
[58] Field of Search ................................ 132/321, 323, 132/325, 326, 327, 328, 329

[56] References Cited

U.S. PATENT DOCUMENTS

| | | |
|---|---|---|
| 1,069,874 | 8/1913 | Hanscom . |
| 1,285,988 | 11/1918 | Gudebrod . |
| 1,287,926 | 12/1918 | Ecaubert . |
| 1,559,320 | 10/1925 | Hirsh ........................................ 132/323 |
| 1,637,153 | 7/1927 | Lawton . |
| 1,839,486 | 1/1932 | Lawton . |
| 1,989,895 | 2/1935 | Van Gilder ............................. 132/321 |
| 2,522,794 | 2/1950 | Medof . |
| 3,511,249 | 5/1970 | Baitz . |
| 3,699,979 | 10/1972 | Muhler . |
| 3,744,499 | 7/1973 | Wells . |
| 3,930,059 | 12/1975 | Wells . |
| 4,008,727 | 2/1977 | Thornton . |
| 4,142,538 | 3/1979 | Thornton ................................ 132/323 |
| 4,450,849 | 5/1984 | Cerceo et al. . |
| 4,832,063 | 5/1989 | Smole . |
| 4,986,288 | 1/1991 | Kent et al. ............................. 132/321 |
| 5,063,948 | 11/1991 | Lloyd . |
| 5,159,943 | 11/1992 | Richards et al. ........................ 132/321 |
| 5,316,028 | 5/1994 | Flemming ............................... 132/329 |
| 5,545,480 | 8/1996 | Lalani .................................... 132/321 |
| 5,566,691 | 10/1996 | Dolan et al. . |
| 5,588,452 | 12/1996 | Peck . |
| 5,765,576 | 6/1998 | Dolan et al. . |
| 5,848,600 | 12/1998 | Bacino et al. . |
| 5,896,867 | 4/1999 | McGaha et al. ....................... 132/321 |

*Primary Examiner*—Gene Mancene
*Assistant Examiner*—Pedro Philogene
*Attorney, Agent, or Firm*—Joseph E. Funk

[57] ABSTRACT

A dental floss having spaced, spherical protruberances along its length that improve the ability to remove unwanted material trapped between teeth, and improve the ability of a user to hold and use the floss.

6 Claims, 1 Drawing Sheet

DENTAL FLOSS

FIELD OF THE INVENTION

The present invention relates to dental floss, and particularly to an improved dental floss having spaced protruberances that improve the ability to remove unwanted material trapped between teeth, and improve the ability of a user to hold and use the floss.

BACKGROUND OF THE INVENTION

Dental floss is a well-known article used to promote oral hygiene by aiding in the removal of particles lodged in the interproximal areas of the teeth. In normal use a segment of dental floss is passed between two adjacent teeth and manipulated to dislodge food and other unwanted particles trapped between the teeth. Dental floss is typically manipulated under tension against the tooth surface being cleaned in such a way that its motion is lateral to longitudinal axis of the floss in an occluogingival direction along the surface of the tooth. Such movement brings it into direct contact with the surface of the tooth from its crown to the gum line. This movement, if successful, is designed to mechanically dislodge particles of food and other matter lodged on the surface the tooth or trapped between two adjacent teeth.

Use of dental floss is very important in reducing plaque on interproximal surfaces of the teeth that cannot be reached by a toothbrush. Since caries typically develop on tooth surfaces where there is an accumulation of plaque, using floss to remove plaque on interproximal surfaces of teeth reduces the likelihood for the development of caries on the interproximal surfaces.

Conventional dental floss is generally made from relatively small diameter filaments woven together into a single elongated strand having uniform dimensions. The surface of the floss is smooth and is sometimes waxed. This makes it difficult for an individual to hold the floss during use because it cannot be tightly grasped and it slips between the user's fingers. This can be very frustrating to the user and can make flossing ineffective. Such smooth, uniform floss also does not function well to clean concave surfaces on a tooth's interproximal surfaces. In addition, smooth, uniform or relatively uniform floss does not function well in the transport and removal of unwanted material after it is successfully dislodged from interproximal regions between the teeth.

There is a need in the art for an improved dental floss that is better able to transport and remove food particles or material that have been successfully dislodged from interproximal regions between the teeth.

There is also a need in the prior art for an improved dental floss that does not easily slide between a user's fingers and is thereby easier to use flossing teeth.

It is a further need in the art for an improved dental floss that is better able to dislodge and remove food particles and other matter that is trapped in concave areas on tooth surfaces where conventional dental floss rides over such matter.

SUMMARY OF THE INVENTION

The previously described needs in the prior art are satisfied by the present invention. The novel dental floss described and claimed herein better facilitates the transport and removal of material dislodged from interproximal regions between the teeth. In addition, the novel dental floss does not easily slide between the fingers of individual using the floss.

Small protruberances are spaced along the dental floss and the surface of these protruberances that meet the floss rise at a relatively steep angle with respect to the longitudinal axis of the floss. The relatively steep angle at which surfaces of the protruberances rise from the longitudinal axis of the floss better remove food particles and other unwanted material from concave depressions on tooth surfaces, and better snare unwanted particles that have been successfully dislodged from interproximal regions between teeth for their transport and removal. In addition, these small, spaced protruberances permit an individual to hold and use the floss without having difficulty in holding the floss due to it sliding between the individual's fingers.

DESCRIPTION OF THE DRAWING

The invention will be better understood upon reading the following Detailed Description in conjunction with the drawings in which.

DETAILED DESCRIPTION OF THE INVENTION

Figure 1:
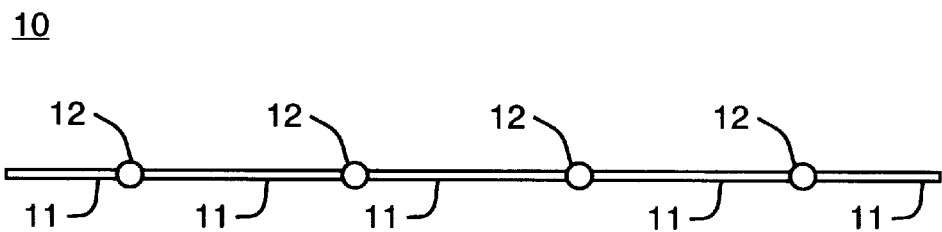
FIG. 1 shows an exemplary apparatus for attaching small, spaced protruberances along the longitudinal axis of the floss during manufacture.

In FIG. 1 is shown a segment of the improved dental floss 10 having a plurality of protruberances 12 attached along the longitudinal axis of standard dental floss 10. After manufacture there are segments 11 of the standard dental floss between each of protruberances 12 as shown. The base dental floss 11 is of a type well-known in the art and is not described in detail herein.

In the preferred embodiment of the invention described herein protruberances 12 are small spherical elements attached to base floss 11 in the order of every one and one-quarter inches to form new floss 10. The diameter of protruberances 12 is preferably in the order of twice the diameter of base floss 11 but may be larger or smaller. As shown in FIG. 1 protruberances 12 are spherical but they may be of different shapes. As seen in FIG. 1, where the outer surface of each of protruberances 12 meets base floss 11 it forms an angle with the longitudinal axis of floss 11 in the order of forty-five degrees, but may be more or less depending upon the ratio of the diameter of protruberances 12 to the diameter of base floss 11. This relatively steep angle is better to snare food particles and other unwanted material that have been successfully dislodged from concave surfaces on teeth and interproximal regions between teeth for its transport and removal without new floss 10 getting stuck between the users teeth as will most likely happen if protruberances 12 meet base floss 11 at an angle of 90 degrees or another very steep angle close to ninety degrees.

Floss 11 may be made from nylon or expanded polytetrafluoroethylene (PTFE). PTFE flosses have a number of advantages over nylon floss including resistance to shredding (i.e. the breaking off of individual strands of the fiber between teeth of a user) and high lubricity. However, due to the high lubricious nature of PTFE floss, it is more difficult for an individual to hold the floss during use because it slides between their fingers. This difficulty is negated by the spaced protruberances 12 along floss 10 in accordance with the teaching of the present invention. Protruberances 12 limit the ability of floss 10 to slide between the fingers of the user. The protruberances 12 also contribute to more cost effective floss use because the user does not have to wrap a number of turns of floss around their fingers to effectively hold the floss, such as must be done in the prior art.

Protruberances 12 may be made from nylon or other material that bonds to the nylon, PTFE or other material from which base floss 11 is made as described with reference to FIG. 2. In addition, protruberances 12 may be created and fastened to base floss 11 in other ways known to those skilled in the art, such as by a wrap, loop, knot, or chemical bonding.

Figure 2:
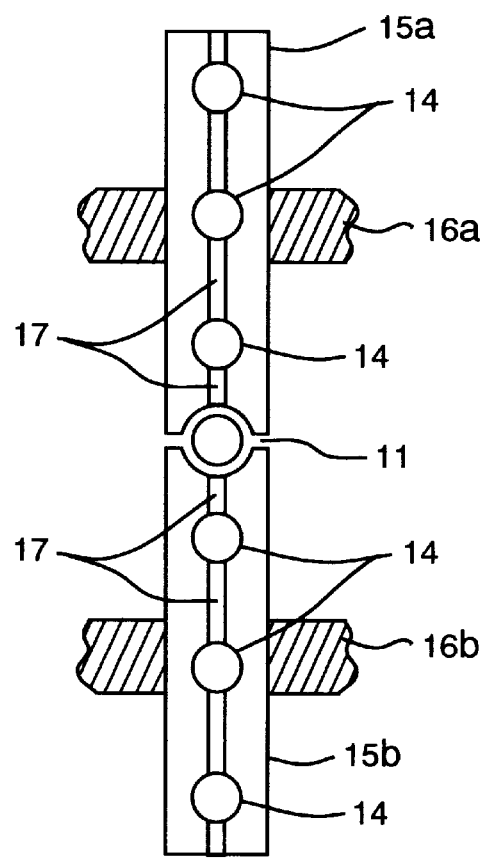
FIG. 2 shows a segment of the improved dental floss with small protruberances spaced along the longitudinal axis of the floss.

In FIG. 2 is shown an exemplary apparatus for attaching protruberances 12 to base floss 11 to create the novel floss 10 in accordance with the teaching of the present invention. Shown are two identical rollers 15a and 15b, each of which is respectively attached to a shaft 16a and 16b. The two shafts 16a and 16b are rotated at the same speed (rpm). The two rollers 15a and 15b each have a groove 17 around their periphery. Rollers 15a and 15b actually touch each other, but are shown slightly spaced in FIG. 2 for ease of presentation. Each groove 17 has a cross sectional shape of a half circle that is slightly smaller than half the cross-section of base floss 11. This permits floss 11, shown in a cross-sectional end view in FIG. 2, to be pinched between rollers 15a and 15b, and as rollers 15a and 15b turn, base floss 11 is drawn between them.

Spaced along groove 17 around the periphery of each of rollers 15a and 15b are hemispherical depressions 14. There are the same number of depressions 14 around the periphery of each of rollers 15a and 15b, and as these rollers turn a depression 14 on roller 15a is always in registration with a depression 14 on roller 15b at the point the two rollers contact each other.

Rollers 15a and 15b are heated and a small drop of molten material, such as molten nylon, is injected into each depression 14 on each of rollers 15a and 15b as the depressions pass under the injection mechanism (not shown). Grooves 17 and hemispherical depressions 14 are coated with a material that inhibits the molten material from bonding to rollers 15a and 15b. The molten material is carried further around the periphery of heated rollers 15a and 15b until it contacts base floss 11 being drawn between the two rollers. At this point the molten material in opposing depressions 14 on rollers 15a and 15b contact each other and floss 11. The molten material fuses to form a spherical protruberance 12 that is fused to base floss 11. As the two rollers turn spherical protruberances 12 are created every one and one-quarter inches along floss 11 to create new floss 10. As desired, protruberances 12 may be spaced at any desired distance along base floss 11 to create new floss 10.

While what has been described hereinabove is the preferred embodiment of the invention, it will be understood that those skilled in the art may make numerous changes without departing from the spirit and scope of the invention.

What is claimed is:

1. A flossing article for facilitating oral prophylaxis comprising:

an elongated dental floss having an outer surface along its length; and a plurality of protruberances of substantially equal size attached to and spaced along said dental floss, said protruberances being of a size and shape that minimizes the possibility of damaging the gums of a user of said flossing article, and said protruberances having a shape the outer surface of which meets the longitudinal axis of said dental floss at a relatively steep angle to facilitate dislodging and removing unwanted particles both on the surface of teeth and lodged between adjacent teeth.

2. The flossing article of claim 1 wherein the shape of said plurality of protruberances aids in preventing said flossing article from sliding between the fingers of a user while flossing their teeth.

3. The flossing article of claim 2 wherein the shape of said protruberances is spherical.

4. The flossing article of claim 1 wherein the shape of said protuberances is spherical.

5. The flossing article of claim 4 wherein the diameter of said spherical protruberances is at least twice the diameter of said elongated dental floss.

6. The flossing article of claim 5 wherein said spherical protruberances are spaced at least one and one-quarter inches.

* * * * *